United States Patent
Löser et al.

(10) Patent No.: US 11,610,672 B2
(45) Date of Patent: Mar. 21, 2023

(54) SYSTEM COMPRISING A MEDICAL APPARATUS AND A REMOTE CONTROL DEVICE, METHOD FOR PAIRING THE REMOTE CONTROL DEVICE AND THE MEDICAL APPARATUS, AND METHOD FOR OPERATING THE MEDICAL APPARATUS

(71) Applicant: TRUMPF MEDIZIN SYSTEME GMBH + CO. KG, Saalfeld (DE)

(72) Inventors: Steffen Löser, Unterwellenborn OT Goßwitz (DE); Matthias Jäger, Rudolstadt (DE); Matthias Köhler, Saalfeld (DE)

(73) Assignee: TRUMPF MEDIZIN SYSTEME GMBH + CO. KG, Saalfeld (DE)

( * ) Notice: Subject to any disclaimer, the term of this patent is extended or adjusted under 35 U.S.C. 154(b) by 162 days.

(21) Appl. No.: 17/072,088

(22) Filed: Oct. 16, 2020

(65) Prior Publication Data
US 2021/0118561 A1   Apr. 22, 2021

(30) Foreign Application Priority Data
Oct. 17, 2019 (EP) ..................................... 19203764

(51) Int. Cl.
*G16H 40/63* (2018.01)
*G08C 17/02* (2006.01)
*A61M 5/172* (2006.01)
(Continued)

(52) U.S. Cl.
CPC ............. *G16H 40/63* (2018.01); *A61G 7/018* (2013.01); *A61M 5/172* (2013.01); *G08C 17/02* (2013.01);
(Continued)

(58) Field of Classification Search
CPC ........ G16H 40/63; G16H 40/67; G08C 17/02; G08C 2201/20; A61G 7/018;
(Continued)

(56) References Cited

U.S. PATENT DOCUMENTS 5,751,595 A    5/1998  Beatty, III et al.
9,173,992 B2   11/2015 Bengtsson et al.
(Continued)

FOREIGN PATENT DOCUMENTS

EP   3005587 A1   4/2016

*Primary Examiner* — Adnan Aziz
(74) *Attorney, Agent, or Firm* — Barnes & Thornburg LLP

(57) ABSTRACT

In a system, a medical apparatus and a remote control device perform a pairing procedure, in which the remote control device sends an identifier of the remote control device, the medical apparatus sends a time-referenced information, the remote control device receives the time-referenced information and generates a first hash key based on the identifier and the time-referenced information, and the medical apparatus receives the identifier and generates a second hash key based on the identifier and the time-referenced information. The second hash key corresponds to the first hash key, wherein, when the pairing has been successfully completed, the remote control device sends an instruction controlling the medical apparatus based on the first hash key, and the medical apparatus accepts the instruction if the first hash key corresponds to the second hash key.

17 Claims, 3 Drawing Sheets

(51) Int. Cl.
*A61G 7/018* (2006.01)
*H04L 9/32* (2006.01)
*A61M 5/142* (2006.01)

(52) U.S. Cl.
CPC ........ *H04L 9/3236* (2013.01); *A61G 2203/12* (2013.01); *A61M 5/142* (2013.01); *A61M 2205/3584* (2013.01); *A61M 2205/581* (2013.01); *A61M 2205/583* (2013.01); *A61M 2205/60* (2013.01); *A61M 2209/01* (2013.01); *G08C 2201/20* (2013.01)

(58) Field of Classification Search
CPC ... A61G 2203/12; A61M 5/172; A61M 5/142; A61M 2205/3584; A61M 2205/581; A61M 2205/583; A61M 2205/60; A61M 2209/01; H04L 9/3236; H04L 9/0643; H04L 9/0838; H04L 9/0866; H04L 9/0872; H04L 2209/88; H04L 63/061; H04W 12/50

See application file for complete search history.

(56) References Cited

U.S. PATENT DOCUMENTS

| | | | | |
|---|---|---|---|---|
| 9,980,140 | B1* | 5/2018 | Spencer | H04W 12/02 |
| 10,350,025 | B1* | 7/2019 | Loyd | A61B 90/90 |
| 2014/0222574 | A1 | 8/2014 | Emigh et al. | |
| 2015/0207626 | A1* | 7/2015 | Neftel | G16H 40/67 |
| | | | | 713/168 |
| 2016/0328958 | A1 | 11/2016 | Ruch et al. | |
| 2017/0093822 | A1 | 3/2017 | Gutierrez et al. | |
| 2017/0201380 | A1 | 7/2017 | Schaap et al. | |
| 2018/0001010 | A1* | 1/2018 | Blümler | G08C 23/04 |
| 2018/0375839 | A1* | 12/2018 | Dattolo | G06F 21/606 |
| 2019/0036688 | A1* | 1/2019 | Wasily | H04L 9/0825 |
| 2020/0082937 | A1* | 3/2020 | Bodurka | H04W 4/50 |
| 2020/0162896 | A1* | 5/2020 | Su | H04W 8/005 |
| 2020/0313872 | A1* | 10/2020 | Mondello | H04L 9/3239 |
| 2021/0045169 | A1* | 2/2021 | Pupakdee | G06F 21/445 |
| 2022/0070221 | A1* | 3/2022 | Labudde | H04L 63/18 |

* cited by examiner

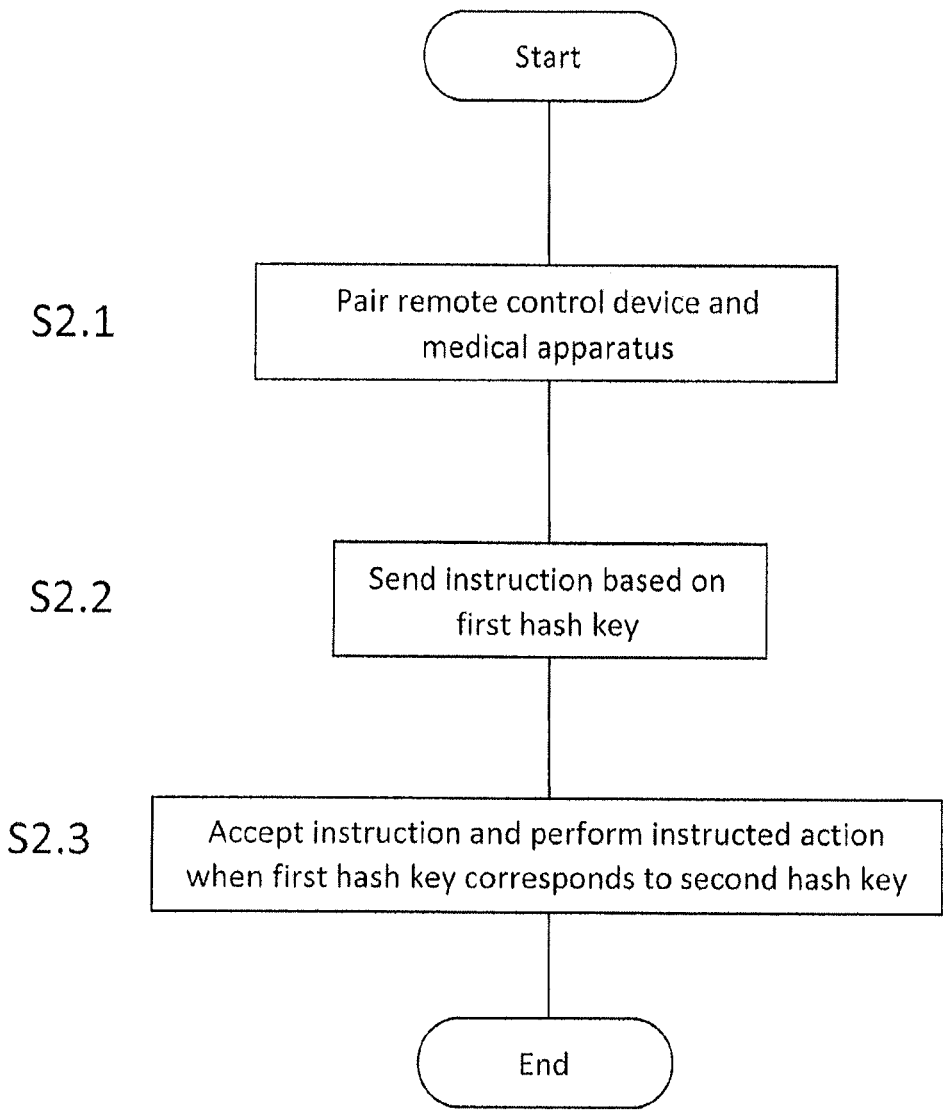

SYSTEM COMPRISING A MEDICAL APPARATUS AND A REMOTE CONTROL DEVICE, METHOD FOR PAIRING THE REMOTE CONTROL DEVICE AND THE MEDICAL APPARATUS, AND METHOD FOR OPERATING THE MEDICAL APPARATUS

CROSS-REFERENCE TO RELATED APPLICATIONS

This application claims the benefit of European Patent Application Serial No. EP19203764.6, filed Oct. 17, 2019, the entire disclosure of which is incorporated herein by reference in its entirety.

TECHNICAL FIELD

The present disclosure relates to a system comprising a medical apparatus and a remote control device, a method for pairing the remote control device and the medical apparatus, and a method for operating the medical apparatus. In particular, the present disclosure discloses an approach for providing a distinctive wireless connection between the remote control device and the medical apparatus.

BACKGROUND

Medical apparatuses may be operated by wireless remote control devices. However, in the field of the medical apparatuses, a distinctive connection between the remote control device and the medical apparatus is important in order to prevent an unintended operation of a medical apparatus by a remote control device being not assigned to that apparatus, e.g., being located in other room, for fulfilling safety requirements. On the other hand, a hardwired configuration of a remote control device for one specific medical apparatus creates problems in operating the medical apparatus in case of replacement of the remote control device.

Therefore, a remote control device suitable for operating the medical apparatus may be paired with a specific one of the medical apparatuses so that this remote control device can only operate this specific medical apparatus. However, the pairing procedure may be elaborate and time consuming due to the request for pressing buttons on the remote control device and on the medical apparatus to confirm the one-to-one relationship.

In order to simplify the pairing process, a pairing procedure has been developed which is initiated by merely pressing a button on the remote control device. EP3005587A1 discloses a pairing procedure initiated by merely pressing one button on the remote control device. Initiated by pressing the button, a pairing request is sent by the remote control device to an operating table; then, a preset device address of the operating table is then sent back from the operating table to the remote control device for establishing pairing of the remote control device and the operating table. However, due to the use of the known preset device address, the pairing between the remote control device and the operating table can easily be manipulated such that a remote control device not being intended to operate a specific operating table can be used for operating this operating table.

Therefore, an object underlying the present disclosure is to remedy the above-mentioned disadvantages and to provide a system of a remote control device and a medical apparatus which can be paired easily in a safe manner.

SUMMARY

The present disclosure includes one or more of the features recited in the appended claims and/or the following features which, alone or in any combination, may comprise patentable subject matter.

According to an aspect of the present disclosure, in a system comprising a medical apparatus and a remote control device for controlling the medical apparatus, the medical apparatus and the remote control device are configured to perform a pairing procedure. In the pairing procedure, the remote control device is configured to send an identifier of the remote control device and the medical apparatus is configured to send a time-referenced information. The remote control device is configured to receive the time-referenced information and to generate and to store a first hash key based on an identifier of the remote control device and the time-referenced information. The medical apparatus is configured to receive the identifier of the remote control device and to generate and to store a second hash key based on the identifier of the remote control device and the time-referenced information. The second hash key corresponds to the first hash key. Further, when the pairing process has been successfully completed, during operation, the remote control device is configured to send an instruction for controlling the medical apparatus based on the first hash key, and the medical apparatus is configured to accept the instruction if the first hash key corresponds to the second hash key.

In this way, the pairing can be easily performed by sending the identifier, i.e., an identifier code, of the remote control device or of a processor of the remote control device, and a time-referenced information of the medical apparatus and by respectively creating and storing the first and the second hash key based on this identifier and this time-referenced information in the remote control device and the medical apparatus. In some embodiments, the time-referenced information may be, e.g. a time stamp generated by the medical apparatus of a current time. The first and the second hash key may either be identical or when not identical but may have a certain relationship.

In some embodiments, when the pairing has been successfully completed and when the instructions for controlling the medical apparatus are based on the first hash key which corresponds to the second hash key, the instructions may be transmitted in a safe manner since a distinctive connection is possible by using the unique identifier of the remote control device and the time-referenced information of the medical apparatus which may also be regarded as being unique. Moreover, since no apparatus-specific data are used for the pairing, manipulation of other remote control devices for using the established pairing may not be possible since the time-referenced information is not known.

In some embodiments of the system, the remote control device comprises a switch, and the remote control device is configured to send a pairing request for initiating a pairing procedure based on the identifier of the remote control device upon an actuation of the switch. Upon provision of such a switch, e.g., actuated by a button of the remote control device, the initiation of the pairing procedure may be possible by pressing the button, wherein simultaneously, the identifier of the remote control device is transmitted so that no further action is necessary.

In some embodiments of the system, the medical apparatus is configured to delete the second hash key in case of a subsequent pairing request. As such, the use of only one remote control device for operating the medical apparatus may be ensured so that no hazardous situation can occur due to an unintended operation of the medical apparatus by another remote control device.

In some embodiments of the system, the first hash key and the second hash key are identical.

In some embodiments, when a controller of the remote control device and a controller of the medical apparatus use the same building rules for generating the hash keys, the first hash key and second hash key may be identically generated in order to provide a simple procedure for generating the hash keys corresponding to each other.

In some embodiments of the system, the remote control device and the medical apparatus may not be configured to send the respective hash key for itself. When the hash keys are not sent, they cannot be detected easily and used abusively.

According to some embodiments of the system, the system may be configured to finish the pairing procedure when a predefined operation code is sent from the remote control device and received by the medical apparatus or when a predefined time expires. In such embodiments, no further action may be required for finishing the pairing procedure. For example, an easy sending of the predefined operation code from the switch or waiting until the predetermined time expires may be sufficient for finishing the pairing procedure.

Some embodiments of the system, the identifier may be a serial number of the remote control device. By the use of the serial number of the remote control device, a unique identifier or identifier code may be easily be determined so that a distinctive connection can easily be established.

According to another aspect of the disclosure, a method for pairing the remote control device and the medical apparatus includes the steps of sending the identifier of the remote control device by the remote control device, receiving the identifier of the remote control device, sending a time-referenced information, and generating the second hash key based on the identifier of the remote control device and the time-referenced information by the medical apparatus. The method further includes receiving the time-referenced information and generating the first hash key based on the identifier of the remote control device and the time-referenced information by the remote control device. In this way, the pairing may be easily performed by sending the identifier of the remote control device or of the processor of the remote control device, and the time-referenced information, e.g. the time stamp of a current time of the medical apparatus, and by respectively generating the first and the second hash key based on this identifier and this time-referenced information in the remote control device and the medical apparatus.

In some embodiments of the method, the method may also include the step of actuating the switch of the remote control device and, thereby, sending the pairing request by the remote control device to initiate the pairing of the remote control device and the medical apparatus. The initiation of the pairing may be easily possible by actuating the switch, e.g., by pressing the button, wherein simultaneously, the identifier of the remote control device is transmitted so that no further action is necessary.

In some embodiments of the method, the identifier of the remote control device is sent along with the pairing request for initiating the pairing. Due to this step, the initiation of the paring may be possible by pressing the button, wherein simultaneously, the identifier of the remote control device is transmitted so that no further action is necessary.

In some embodiments of the method, the method may further include the step of finishing the pairing by sending a predefined operation code from the remote control device and receiving the predefined operation code by the medical apparatus, or by elapsing a predefined time period. In this way, the pairing may be easily finished without any further action of an operator.

In some embodiments of the method, the method may include the step of signaling the finish of the pairing by an acoustic or visual signal. In this way, the operator may be clearly informed that the pairing is finished and the remote control device can be used for operating the medical apparatus.

In some embodiments of the method, the first hash key and the second hash key may be identically generated. When the identical first hash key and second hash key are generated, the controller of the remote control device and the controller of the medical apparatus may use the same building rule in order to provide a simple procedure for generating the hash keys identically.

In some embodiments of the method, the second hash key may be deleted by the medical apparatus in case of a subsequent pairing request. In such an embodiment, the use of only one remote control device for operating the medical apparatus may be ensured so that no hazardous situation can occur do to an unintended operation of the medical apparatus by another remote control device.

According to another aspect of the present disclosure, a method includes the steps of performing a pairing, sending an instruction for a specific operation of the medical apparatus based on the first hash key by the remote control device, and accepting the instruction by the medical apparatus when the first hash key corresponds to the second hash key.

According to this aspect, after the pairing procedure, when the instructions for controlling the medical apparatus are based on the first hash key which corresponds to the second hash key, the instructions may be transmitted in a safe manner since a distinctive connection may be possible by using the unique identifier of the remote control device and the time stamp of the initiation of the pairing which may also be unique. Moreover, since no apparatus-specific data are used for the pairing, manipulation of another remote control device for using the established pairing may not be possible since the time stamp is not known.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 3 shows a flow chart of a method for operating the medical device by the remote control device of the system of FIG. 1.

DETAILED DESCRIPTION

Figure 1:
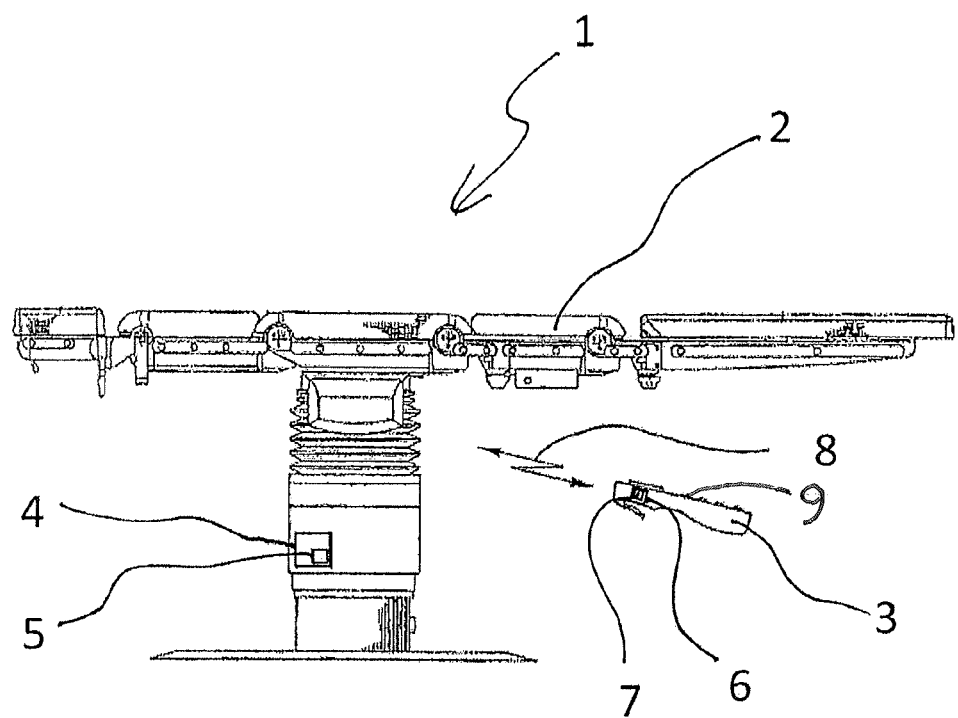
FIG. 1 shows a system comprising a medical apparatus and a remote control device.

FIG. 1 shows a system 1 comprising a medical apparatus 2 and a remote control device 3 for controlling the medical apparatus 2. In this embodiment, the medical apparatus 2 is formed by an operating table; however, in other embodiments, the medical apparatus 2 can be formed by, e.g., a hospital bed or an infusion pump controlled by a respective remote control device 3.

The medical apparatus 2 is provided with a first controller 4 joined to a first transmitting-receiving device 5 and the remote control device 3 is provided with a second controller 6 joined to a second transmitting-receiving device 7. The first transmitting-receiving device 5 and the second transmitting-receiving device are configured to perform data exchange 8 with each other.

In order to be enabled to perform the data exchange 8 for operating the medical device 2 by the remote control device 3, the medical apparatus 2 and the remote control device 3 are configured to perform a pairing procedure.

The remote control device 3 comprises a switch 9 for input of an instruction for initiating the pairing procedure, i.e., for sending a paring request. In an alternative embodiment, the switch is not provided but, under specific conditions, the remote control device 3 sends a pairing request, e.g., cyclically.

The remote control device 3 is configured to send an identifier of the remote control device 3 in the pairing procedure. The identifier is a serial number of the remote control device 3; however, alternatively, a serial number of the second controller 6 or another specific identifier of the remote control device 3 can be sent.

Further, the medical device 2 is configured to send a time-referenced information. In the present embodiment, the medical device 2 sends a timestamp of a current apparatus time when receiving the pairing request. Alternatively, another time-referenced signal, e.g., a timestamp including a certain delay, can be sent. Further alternatively, the time-referenced signal is not sent when receiving the pairing request but it is sent cyclically when no pairing is established.

Furthermore, the remote control device 3 is configured to receive the time-referenced information and to generate and to store a first hash key based on the identifier of the remote control device 3 and the time-referenced information.

Moreover, the medical apparatus 2 is configured to receive the identifier of the remote control device 3 and to generate and to store a second hash key based on the identifier of the remote control device 3 and the time-referenced information.

The medical device 2 and the remote control device 3 are configured such that the second hash key generated by the medical apparatus 2 corresponds to the first hash key generated by the remote control device 3. The first hash key and the second hash key are identical. Alternatively, the first hash key and the second hash key are not identical but provided in a specific relationship.

The medical apparatus 2 and the remote control device 3 are configured not to send the respectively generated hash key as a single data set in order to avoid detection and abusively use of the hash keys. In another embodiment, e.g., in case of an implementation without safety-critical functions, the hash key is sent, e.g., as part of a data set of an instruction.

When the pairing procedure is successfully completed, the remote control device 3 is configured to send an instruction for controlling the medical apparatus 2 based on the first hash key and the medical apparatus 2 is configured to accept the instruction if the first hash key corresponds to the second hash key.

The remote control 3 is configured such that, based on the instruction for initiating the pairing procedure, the remote control 3 sends the pairing request for initiating the paring procedure along with the identifier of the remote control device 3 upon an actuation of the switch 9. Alternatively, the transmission of the identifier of the remote control device 3 occurs at another time.

In case that a subsequent pairing request occurs, the medical apparatus 2 is configured to delete the second hash key. This behavior enables an unambiguous correlation between the remote control device 3 and the medical apparatus 2. Alternatively, the second hash key is not deleted until a specific request for deleting the second hash key at the medical device 2 has been received.

The system is configured to finish the pairing procedure when a predefined operation code is sent from the remote control device 3 and received by the medical apparatus 2, or when a predefined time expires. Alternatively, the pairing procedure has to be finished actively by, e.g. actuating a release button.

Figure 2:
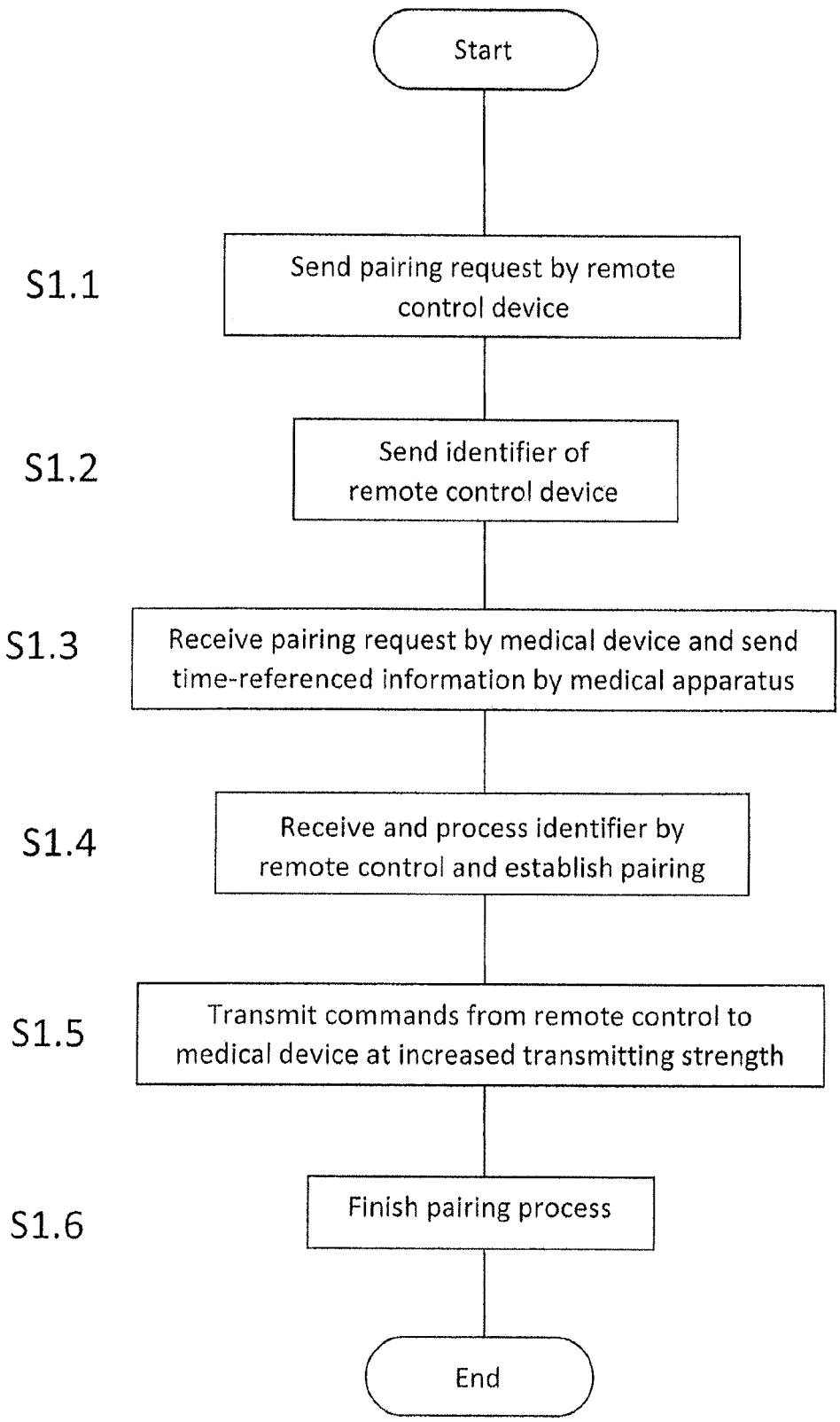
FIG. 2 shows a flow chart of method for pairing the remote control device and the medical apparatus of the system of FIG. 1.

FIG. 2 shows a flow chart of a method for pairing the remote control device 3 and the medical apparatus 2.

In use, in order to perform pairing between the remote control device 3 and the medical apparatus 2, the pairing procedure has to be initiated. This is done in step S1.1, e.g., by actuating the switch 9 of the remote control device 3 and by, thereby, sending a pairing request by the remote control device 3.

In the pairing procedure, in step S1.2, the remote control device 3 sends the identifier of the remote control device 3, as the case may be, along with the pairing request.

In Step S1.3, the medical apparatus 2 receives the pairing request and, initiated by the pairing request, sends a time-referenced information. For signaling the pairing procedure, the operating table plays a sound and all buttons of the remote control 3 are blinking. Alternatively, other signals are respectively possible.

In step S1.4, the remote control device 3 receives the time-referenced information of the medical apparatus 2 and generates a first hash key based on the identifier of the remote control device 3 and the time-referenced information.

Further, in step S1.5, the medical apparatus 2 receives the identifier of the remote control device 3 and generates a second hash key based on the identifier of the remote control device 3 and the time-referenced information. The medical apparatus 2 uses the time stamp of the current apparatus time of the medical apparatus 2 for creating the first hash key. Alternatively, a time-referenced information different from the time stamp of the current apparatus time is used.

The first hash key and the second hash key are generated by means of the same building rules and, therefore, they are identical. In another embodiment, the hash keys are not generated such that they are identical, however, they correspond to one another.

In step S1.6, the pairing procedure is finished either by sending a predefined operation code based on the first hash key from the remote control device 3 and by receiving the predefined operation code by the medical apparatus 2 or by allowing a predefined time to elapse. In this embodiment, the time is set to 30 seconds, however, alternatively another time can be set, e.g. 1 minute. In further alternative embodiments, only one of the predefined operation code and the time criteria is used. The medical apparatus 2 does not send back a confirmation signal that the pairing is completed. Alternatively, the medical apparatus 2 sends back the confirmation signal.

The finish of the pairing is signaled by an acoustic signal. In other embodiments, the finish of the pairing is signaled by a visual signal or by a combination of the acoustic and the visual signal.

If the pairing was successful, the buttons of the remote control device 3 stop blinking and are turned on permanently and the pairing is finished. The predefined operation code is generated by the remote control device 3 automatically as acknowledge and as indication for the medical apparatus 2 that the remote is paired. Until predefined operation code is received, the medical apparatus 2 sends the time-referenced information continuously. Alternatively, the time-referenced information is sent in another manner, e.g., cyclically.

The second hash key generated by the medical apparatus 2 is deleted by the medical apparatus 2 in case of a subsequent pairing request of anyone of a suitable remote control device 3. On the one hand, such a subsequent pairing request can be sent by the most recently paired remote control device 3, e.g. in case of a loss of the hash key by the remote control device due to pairing with another medical apparatus 2 or due to running out energy of a battery. On the other hand, the subsequent pairing request can be sent by another remote control device 3 if, e.g. the paired remote control device 3 got lost or damaged.

FIG. 3 shows a flow chart of a method for operating the medical device 2 by the remote control device 3.

For operating the medical apparatus 2 by the remote control device 3, in step 2.1, the pairing of the medical apparatus 2 and the remote control device 3 is established.

After the successful pairing, when an operator instructs a certain operation of the medical apparatus 2, in step 2.2, the remote control device 3 sends an instruction based on the first hash key. The instruction is a data set including the hash key and an instruction for the certain operation of the medical apparatus 2. Alternatively, the hash key is not included but a data set according to the hash key.

In step 2.3, the medical apparatus 2 accepts the instruction when the first hash key of the remote control device 3 corresponds to the second hash key of the medical apparatus 2 and performs the instructed operation.

In case that the first hash key and the second hash key do not correspond to one another, no action of the medical apparatus 2 is performed.

Although this disclosure refers to specific embodiments, it will be understood by those skilled in the art that various changes in form and detail may be made without departing from the subject matter set forth in the accompanying claims. The present disclosure has been illustrated and described in detail in the drawing and the foregoing description, such illustration and description are to be considered illustrative or exemplary and not restrictive. The invention is not limited to the disclosed embodiments. From reading the present disclosure, other modifications will be apparent to a person skilled in the art. Such modifications may involve other features, which are already known in the art and may be used instead of or in addition to features already described herein. In the claims, the word "comprising" does not exclude other elements or steps, and the indefinite article "a" or "an" does not exclude a plurality.

The invention claimed is:

1. A system comprising
a medical apparatus and a remote control device for controlling the medical apparatus, the medical apparatus and the remote control device being configured to perform a pairing procedure to establish a distinctive connection between the remote control device and the medical apparatus, in which,
the remote control device is configured to send an identifier of the remote control device with a pairing request,
the medical apparatus is configured to, in response to the pairing request, send a time-referenced information to the remote control device,
the remote control device is configured to receive the time-referenced information and to generate and to store a first hash key based on the identifier of the remote control device and the time-referenced information from the medical apparatus, and
the medical apparatus is configured to receive the identifier of the remote control device and to generate and to store a second hash key based on the identifier of the remote control device and the time-referenced information sent to the remote control device, wherein
the medical apparatus and the remote control device are further configured such that the second hash key generated by the medical apparatus corresponds to the first hash key generated by the remote control device,
wherein, when the pairing has been successfully completed,
the remote control device is configured to send the first hash key and an instruction for controlling the medical apparatus based on the first hash key;
the medical apparatus is configured to (i) receive the first hash key and the instruction, and (ii) accept and act on the instruction if the first hash key corresponds to the second hash key, and
the medical apparatus is configured to delete the second hash key if another pairing request is received from any other remote control device.

2. The system of claim 1, wherein the remote control device comprises a switch, and the remote control device is configured to send a paring request for initiating a paring procedure based on the identifier of the remote control device upon an actuation of the switch.

3. The system of claim 2, wherein the medical apparatus is configured to delete the second hash key in case of a subsequent pairing request.

4. The system of claim 3, wherein the first hash key and the second hash key are identical.

5. The system of claim 4, wherein the system is configured to finish the pairing procedure when a predefined operation code is sent from the remote control device and received by the medical apparatus, or when a predefined time expires.

6. The system of claim 5, wherein the identifier is a serial number of the remote control device.

7. The system of claim 1, wherein the medical apparatus is configured to delete the second hash key in case of a subsequent pairing request by the remote control apparatus the medical apparatus is paired with.

8. The system of claim 1, wherein the first hash key and the second hash key are identical.

9. The system of claim 1, wherein the remote control device and the medical apparatus are configured not to send the respective hash key.

10. The system of claim 1, wherein the system is configured to finish the pairing procedure when a predefined operation code is sent from the remote control device and received by the medical apparatus, or when a predefined time expires.

11. The system of claim 1, wherein the identifier is a serial number of the remote control device.

12. A method for operating a medical apparatus by a distinctive remote control device, including the steps:
- sending an identifier of the remote control device by the remote control device with a pairing request;
- receiving the identifier of the remote control device with the pairing request, sending a time-referenced information, and generating and storing a second hash key based on the identifier of the remote control device and the time-referenced information by the medical apparatus;
- receiving the time-referenced information and generating and storing a first hash key based on the identifier of the remote control device and the time-referenced information by the remote control device;
- wherein when the pairing has been successfully completed,
- sending the first hash key and an instruction for a specific operation of the medical apparatus based on the first hash key by the remote control device;
- receiving the first hash key and the instruction by the medical apparatus;
- accepting the instruction by the medical apparatus and performing the specific operation according to the instruction when the first hash key corresponds to the second hash key; and
- deleting the second hash key if another pairing request is received from any other remote control device by the medical apparatus.

13. The method of claim 12, including the step of actuating a switch of the remote control device and, thereby, sending the pairing request by the remote control device to initiate the pairing of the remote control device and the medical apparatus.

14. The method of claim 13, including the step of finishing the pairing procedure by sending a predefined operation code by the remote control device and receiving the predefined operation code by the medical apparatus, or by elapsing a predefined time period.

15. The method of claim 14, including the step of signaling the finish of the pairing by an acoustic or visual signal.

16. The method of claim 15, wherein the first hash key and the second hash key are identically generated.

17. The method of claim 16, wherein the second hash key is deleted by the medical apparatus in case of a subsequent pairing request by the remote control apparatus the medical apparatus is paired with.

* * * * *